United States Patent [19]

Cohen

[11] Patent Number: 5,101,040

[45] Date of Patent: Mar. 31, 1992

[54] PROCESS FOR THE INDUSTRIAL PREPARATION OF 4-CHLORO-3-SULFAMOYL-N-(2,3-DIHYDRO-2-METHYL-1H-INDOL-1-YL)BENZAMIDE

[75] Inventor: Armand Cohen, Bolbec, France

[73] Assignee: Adir Et Compagnie, Cedex, France

[21] Appl. No.: 704,308

[22] Filed: May 22, 1991

[30] Foreign Application Priority Data

Jun. 14, 1990 [FR] France .............................. 90 07386

[51] Int. Cl.⁵ ............................................ C07D 209/08
[52] U.S. Cl. ................................... 548/483; 548/469
[58] Field of Search ........................................ 548/483

[56] References Cited

U.S. PATENT DOCUMENTS

| 3,565,911 | 2/1971 | Beregi | 548/483 |
| 4,570,001 | 2/1986 | Auerbach | 548/483 |

FOREIGN PATENT DOCUMENTS

| 0068239 | 1/1983 | European Pat. Off. | 548/483 |
| 0124766 | 7/1983 | Japan | 548/483 |
| 0124767 | 7/1983 | Japan | 548/483 |
| 1203691 | 9/1970 | United Kingdom | 548/483 |

Primary Examiner—Mary C. Lee
Assistant Examiner—Jacqueline Haley
Attorney, Agent, or Firm—Gordon W. Hueschen

[57] ABSTRACT

The invention relates to a new process for the industrial preparation of 4-chloro-3-sulfamoyl-N-(2,3-dihydro-2-methyl-1H-indol-1-yl)benzamide from monochloramine and 2,3-dihydro-2-methyl-1H-indole.

6 Claims, No Drawings

PROCESS FOR THE INDUSTRIAL PREPARATION OF 4-CHLORO-3-SULFAMOYL-N-(2,3-DIHYDRO-2-METHYL-1H-INDOL-1-YL)BENZAMIDE

The present invention relates to a new process for the industrial preparation of 4-chloro-3-sulfamoyl-N-(2,3-dihydro-2-mathyl-1H-indol-1-yl)benzamide.

This compound, also known under the INN of indapamide, possesses very advantageous pharmacological properties. It is endowed, in particular, with antihypertensive properties and is used for the treatment of essential arterial hypertension.

Several methods of preparation of this compound are already known. However, the processes already described in the literature do not always enable indapamide to be obtained with satisfactory purity or in good yield. In addition, some steps of these processes can cause problems at the industrial level.

The process for the preparation of 4-chloro-3-sulfamoyl-N-(2,3-dihydro-2-methyl-1H-iniol-1-yl)benzamide described in Patent FR 2,003,311 consists in obtaining this compound by reacting 4-chloro-3-sulfamoylbenzoyl chloride with 1-amino-2,3-dihydro-2-methylindole. The latter compound is prepared according to the process of J. B. Wright and R. E. Willette (J. Med. and Pharm. Chem. 5 811 (1962)), which comprises reduction of the N-nitroso analog. The yield of the different steps of this process is unsatisfactory.

Moreover, this synthesis process leads to the production of by-products, in particular nitrosamine derivatives, which are potentially toxic compounds.

Patent JP 54.030,159 describes a process for the preparation of indapamide from 4-chloro-3-sulfamoyl-N-(2-methyl-1-indolyl)benzamide, which is converted to indapamide after reduction.

This process closely resembles the one above and also leads to the formation of a large number of by-products, and several purifications are necessary in order to obtain a pharmaceutical grade product.

Another process for the preparation of indapamide is described in Patent EP 54,892. This process consists in cyclizing 1-allyl-1-phenyl-2-(3-sulfamoyl-4-chlorobenzoyl) hydrazine in the presence of Lewis or Bronsted acids. This cyclization also leads to the formation of a large number of by-products, and the yield of this process is unsatisfactory.

In view of the therapeutic importance of indapamide and of the absence of an industrial process enabling it to be obtained with satisfactory purity, in good yield and, if possible, from inexpensive and commercially available starting materials, more detailed research was undertaken and led to the discovery of a new process for the preparation of 4-chloro-3-sulfamoyl-N-(2,3-dihydro-2-methyl-1H-indol-1-yl-)benzamide. The final stage of this process resembles that described in Patent FR 2,003,311, but it has two great advantages: it requires fewer steps, and the preparation of 1-amino-2,3-dihydro-2-methyl-1H-indole is carried out without the formation of the N-nitroso analog. The industrial application of this process is hence very advantageous.

The subject of the present invention is, more especially, a process for the industrial synthesis of 4-chloro-3-sulfamoyl-N-(2,3-dihydro-2-methyl-1H-indol-1-yl)benzamide, the compound of formula I:

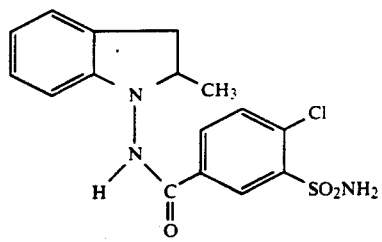

(I)

wherein a solution of ammonium hydroxide and ammonium chloride is reacted with an aqueous solution of sodium hypochlorite at a temperature of between −10° C. and −5° C. in an alkaline medium, and the monochloramine thereby formed is reacted with 2,3-dihydro-2-methyl-1H-indole, the compound of formula II:

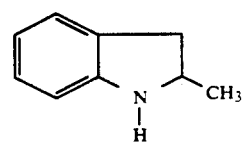

(II)

in solution in a low molecular weight ($C_1$–$C_5$)) aliphatic alcohol, in a suitable reactor equipped with a coaxial vane type stirrer, at a temperature of between 30° C. and 80° C. and in an alkaline medium, and the 1-amino-2,3-dihydro-2-methyl-1H-indole, the compound of formula III:

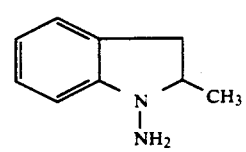

(III)

is thereafter separated from the reaction medium and reacted in the form of a base or salt, in solution in tetrahydrofuran or in an alcoholic medium and in the presence of an acid-acceptor with 4-chloro-3-sulfamoylbenzoyl chloride, the compound of the formula IV:

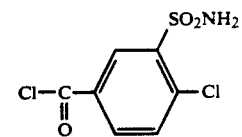

(IV)

at a temperature of between 20° and 30° C. to form the compound of formula I.

The ratio of the molar concentrations of ammonium hydroxide and ammonium chloride to sodium hypochlorite is approximately 2.5 to 3, and the ratio of the molar concentrations of ammonium chloride to ammonium hydroxide is approximately 0.50 to 0.80.

The reaction of monochloramine with 2,3-dihydro--methyl-1H-indole is performed in continuous fashion, in the heated stated and in the presence of an aqueous sodium hydroxide solution.

The concentration of the alcoholic solution of 2,3-dihydro-2-methyl-1H-indole should be between 0.5 and 2 moles/l, and preferably from 0.5 to 1 mole/l. As an alcoholic solvent, methanol or ethanol may preferably be used. The reaction of 2,3-dihydro-2-methyl-1H-indole with chloramine is carried out at a pH of between 13 and 14.

The reaction of monochloramine with 2,3-dihydro-2-methyl-1H-indole is carried out at a temperature of between 30° C. and 80° C., and preferably between 40° C. and 65° C.

At the end of the reaction, the 1-amino-2,3-dihydro-2-methyl-1H-indole may be isolated in the following manner:

When the concentration of 2,3-dihydro-2-methyl-1H-indole used for the reaction is greater than 1 mole/l, the reaction medium can first be allowed to settle in order to recover the organic phase, and the aqueous phase can then be extracted with toluene. The organic phases are then combined and evaporated to dryness to obtain the expected product.

In the case where the concentration of 2,3-dihydro-2-methyl-1H-indole used for the preparation of 1-amino-2,3-dihydro-2-methyl-1H-indole is less than 1 mole/l, the reaction medium is extracted directly with toluene.

The 1-amino-2,3-dihydro-2-methyl-1H-indole thereby obtained may be purified on a (distillation) column and then salified before being used for the preparation of indapamide. Preferably, hydrochloric acid or methanesulfonic acid may be used for the salification.

The reaction of 1-amino-2,3-dihydro-2-methyl-1H-indole with 4-chloro-3-sulfamoylbenzoyl chloride is performed in the presence of an excess of triethylamine. As a reaction solvent, tetrahydrofuran or another chemically equivalent solvent may be used.

A detailed description of the implementation of the process of the invention is given below without implied limitation.

EXAMPLE 1

Preparation of
1-amino-2,3-dihydro-2-methyl-1H-indole

A solution of sodium hypochlorite assaying at 48° chlorometric strength and a solution containing 3.60 moles/l of ammonia and 2.38 moles/l of ammonium chloride are introduced in continuous fashion and with stirring into a reactor ($R_1$) at the rate of 10.53 g and 8.79 g/min, respectively.

The temperature in the reactor $R_1$ is maintained at between $-8°$ and $-10°$ C., and the pH of the reaction is in the region of 10.

At the outlet of $R_1$, a monochloramine solution is obtained, which is introduced into a cylindrical reactor ($R_2$) vigorously stirred by means of a coaxial vane type stirrer.

Into the reactor $R_2$, an alcoholic solution of 2,3-dihydro-2-methyl-1H-indole (C = 1 mole/l; total Q = 2.415 g) is introduced also, at a flow rate of 11.08 g/min, and 30% strength aqueous sodium hydroxide solution at a flow rate of 7.95 g/min. The latter solution is used to maintain the pH of the reaction medium at approximately 13.5. The reaction temperature is 60° C.

At the end of the reaction, after approximately 4 hours, the reaction medium is allowed to settle. The organic phase (=800 g) is recovered and the aqueous phase is thereafter extracted a first time with 750 ml of toluene and a second time with 300 ml of toluene.

The organic phases are combined and the toluene is removed. The evaporation residue is then distilled on a column to obtain pure 1-amino-2,3-dihydro-2-methyl-1H-indole.

Yield: 85%
Melting point: 37-38° C.

The 1-amino-2,3-dihyiro-2-methyl-1H-indole is salified with an appropriate quantity of methanesulfonic acid to obtain 1-amino-2,3-dihydro-2-methyl-1H-indole mesylate.

Melting point (Kofler): 165-172° C.

EXAMPLE 2

Preparation of
3-aminosulfonyl-4-chloro-N-(2,3-dihydro-2-methyl-1H-indol-1-yl)benzamide A reactor ($R_3$), purged with nitrogen, is charged with 800 ml of tetrahydrofuran and 0.2045 mole of 1-amino-2,3-dihydro-2-methyl-1H-indole mesylate. 0.4328 mole of triethylamine is then introduced in the course of 10 minutes. The reaction solution is then stirred at 18-20° C. for 30 minutes. 0.2050 mole of 4-chloro-3-sulfamoyl-benzoyl chloride, in solution in 400 ml of tetrahydrofuran, is then introduced dropwise in the course of 1 h 45 min.

The reaction medium is left stirring for 3 hours at 24-30° C. and 0.5 g of Noir $CN_1$ charcoal is then added. The mixture is filtered and the filtrate is concentrated.

The evaporation residue is then recrystallized in isopropanol.

Yield: 80.5%
Purity (HPLC): 99.98%

I claim:

1. A process for the preparation of 4-chloro-3-sulfamoyl-N-(2,3-dihydro-2-methyl-1H-indol-1-yl)-benzamide, the compound of formula I:

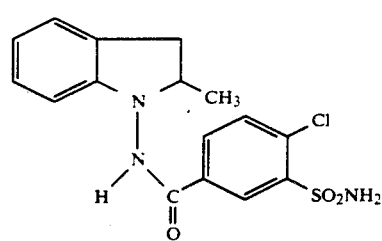

(I)

wherein a solution of ammonium hydroxide and ammonium chloride is reacted with an aqueous solution of sodium hypochlorite at a temperature of between $-10°$ C. and $-5°$ C. in an alkaline medium, and the monochloramine thereby formed is reacted with 2,3-dihydro-2-methyl-1H-indole, the compound of formula II:

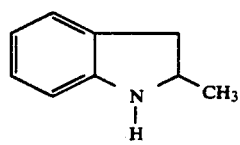

(II)

in solution in a low molecular weight ($C_1$–$C_5$) aliphatic alcohol, at a temperature of between 30° C. and 80° C. and in an alkaline medium, and the 1-amino-2,3-dihydro-2-methyl-1H-indole, the compound of formula III:

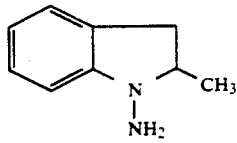

thereby formed, is thereafter separated and reacted in the form of a base or salt, in solution in tetrahydrofuran or in an alcoholic medium and in the presence of an acid-acceptor with 4-chloro-3-sulfamoylbenzoyl chloride, the compound of the formula IV:

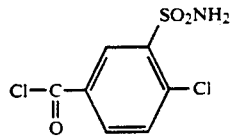

at a temperature of between 20° C. and 30° C. to form the compound of formula I.

2. The process as claimed in claim 1, wherein the 2,3-dihydro-2-methyl-1H-indole is in solution in ethanol.

3. The process as claimed in claim 1, wherein the concentration of the alcoholic solution of 2,3-dihydro--methyl-1H-indole is from 0.5 to 1 mole/l.

4. The process as claimed in claim 1, wherein the reaction of monochloramine with 2,3-dihydro-2-methyl-1H-indole is carried out at a pH of between 13 and 14.

5. The process as claimed in claim 1, wherein the reaction of monochloramine with 2,3-dihydro-2-methyl-1H-indole is carried out at a temperature of between 40 and 5° C..

6. The process as claimed in claim 1, wherein -amino-2,3-dihydro-2-methyl-1H-indole is reacted in the form of a hydrochloride or mesylate with 4-chloro-3-sulfamoylbenzoyl chloride.

* * * * *

UNITED STATES PATENT AND TRADEMARK OFFICE
CERTIFICATE OF CORRECTION

PATENT NO. : 5,101,040

DATED : May 22, 1991

INVENTOR(S) : Armand Cohen

It is certified that error appears in the above-identified patent and that said Letters Patent is hereby corrected as shown below:

```
Column 1, line 9;  "-2-mathyl-" should read -- -2-methyl- --.
Column 1, approximately line 23; "-iniol-" should read
   -- -indol- --.
Column 1, line 36; "-N-(?-" should read -- -N-(2- --.
Column 2, line 61; "-dihydro--" should read -- dihydro- --.
Column 2, line 62; "-methyl-" should read -- 2-methyl- --.
Column 2, line 63; "heated stated" should read --heated state--.
Column 4, line 25; "CN₁charcoal" should read --CN₁®charcoal--.
Column 6, line 14; "dihydro--" should read -- dihydro- --.
Column 6, line 15; "-methyl-" should read -- 2-methyl- --.
Column 6  line 23; "5° C.." should read -- 65° C. --.
Column 6, line 24; "wherein amino-" should read
   -- wherein 1-amino- --.
```

Signed and Sealed this

Tenth Day of August, 1993

Attest:

MICHAEL K. KIRK

Attesting Officer

Acting Commissioner of Patents and Trademarks